United States Patent [19]
Ashe

[11] 3,955,087
[45] May 4, 1976

[54] APPARATUS FOR MEASURING MOISTURE IN MOVING BULK MATERIAL USING A LITHIUM-7 RADIATION SOURCE

[75] Inventor: John B. Ashe, Palatine, Ill.

[73] Assignee: G. D. Searle & Co., Skokie, Ill.

[22] Filed: Sept. 4, 1974

[21] Appl. No.: 503,487

[52] U.S. Cl. .............................. 250/360; 250/390; 250/499
[51] Int. Cl.² ......................................... G01N 23/12
[58] Field of Search ........... 250/358, 359, 360, 390, 250/391, 392, 499

[56] References Cited
UNITED STATES PATENTS

| | | | |
|---|---|---|---|
| 3,532,883 | 10/1970 | Dresia et al. | 250/358 |
| 3,716,711 | 2/1973 | Olesen | 250/390 |
| 3,761,712 | 9/1973 | Listerman | 250/392 X |

Primary Examiner—Archie R. Borchelt
Attorney, Agent, or Firm—Walter C. Ramm; Peter J. Sgarbossa; Helmuth Wegner

[57] ABSTRACT

A nucleonic device for measuring the moisture content of bulk materials using a radioisotopic fast-neutron source such as lithium-7 admixed with an alpha-particle emitter, such as americium-241, as a means of minimizing the thickness of the layer of bulk material required proximate to the moisture sensor for a neutron-reflection moisture gauge for proper operation of said gauge. Minimization of the required thickness of the bulk material permits use of a neutron-reflection moisture gauge for measurements of bulk materials on lightly-loaded belts and other types of conveyors where measurements have previously been impracticable.

18 Claims, 2 Drawing Figures

APPARATUS FOR MEASURING MOISTURE IN MOVING BULK MATERIAL USING A LITHIUM-7 RADIATION SOURCE

The present invention relates to a type of device known as a neutron-reflection moisture gauge for use in measuring the moisture content of bulk material. A neutron-reflection moisture gauge employs a moisture sensor and a meter or other means of indicating the moisture content of a volume of bulk material in the vicinity of the sensor. The moisture sensor may be mounted on the wall of a bin or hopper to measure the moisture content of bulk material contained therein, or the sensor may be placed next to a belt or other type of conveyor to measure the moisture content of bulk material transported thereon. The bulk material being measured is typically transported from one location to another through the use of a conveyor belt system. Typical commercial applications requiring moisture measurement of bulk materials are in the extraction of coal, ore, or other minerals from mines, the pricing of sand for use in concrete, and in determining the condition of grain and grain products, e.g. flour, and other food products, such as sugar and coffee. The utility of the neutron-reflection moisture gauge for measurement of moisture in bulk materials in bins or hoppers is well established. The utility of such gauges for measurements on materials on belts or other types of conveyors has heretofore been severely limited, primarily because most conveyors cannot be loaded with the depth of material needed to assure proper operation of conventional neutron-reflection moisture gauges. In addition, the physical configuration of conveyor systems is typically limited to some degree by weight considerations or dimensional limitations. This is particularly true in the applications of coal and ore extraction where a belt conveyor system must fit into a mining tunnel.

Conventional devices for use in measuring the moisture content of bulk material register large errors in moisture readings due to variations in the geometrical configuration of the bulk material moving past the moisture measurement devices, whether movement is by conveyor or by the fluctuating level in or passage of material through a storage bin. That is, the cross-sectional geometric configuration of the bulk material is not uniform and varies considerably. The magnitude and frequency of such errors increases with the size of the discrete particles making up the bulk material. That is, greater errors are entailed in the moisture measurement of ore, which is extracted from mines in the form of rocks having dimensions of several inches than is typically encountered in the measurement of granular substances, such as sand. Another variable which will tend to increase the errors due to geometric distribution of the bulk material is the cohesiveness of the material in the presence of water. For example, flour transported in a conveyor system and including a high moisture content will tend to form into large lumps, which increases the probability of variation of geometrical distribution. Gravel, on the other hand, would not exhibit this tendency to such a great extent.

Several attempts have been made to eliminate errors due to the inconsistency of geometrical distribution of a moving bulk material. For example, material moving on a conveyor belt may be ploughed. That is, a barrier is positioned over the conveyor belt which will block the passage of material extending above a predetermined height. This is quite unsatisfactory, however, because material is forced off of the conveyor belt into the surrounding area and because jamming of the conveyor belt occurs where the material is transported in large rigid discrete units, such as the rock mined in ore extraction. Ploughing also tends to compact the bulk material. This may be deleterious to subsequent processing of the material.

Accordingly, it is an object of the present invention to provide a gauge for measuring the moisture content of bulk material in a manner which is insensitive to variations in the geometrical distribution of the bulk material. It is a further object of the invention to provide a moisture measurement device which does not require a density measurement gauge in order to produce reliable results. Such a moisture measurement gauge combined with a density measurement gauge is typified in U.S. Pat. No. 3,748,473. The addition of a density measurement gauge as a necessary adjunct to moisture measurement, while compensating to some extent for variation in geometrical distribution of bulk material, necessarily increases greatly the expense of moisture determinations.

It is a further object of the invention to provide moisture measurement with the elimination of errors due to inconsistencies in the geometric distribution of bulk material without forcing some of the bulk material off of the transport system which is used, such as occurs when a conveyor belt is ploughed. Among the considerations which militate against plowing to achieve uniform thickness of material on a conveyor are the following:

i. Coarsely granular material, or material which contains large lumps cannot be plowed smoothly
ii. Plowing may cause undesirable changes in the state of compaction of the material
iii. Some materials, especially those which are finely divided and quite moist, will adhere to the plow; and the resulting build-up of material will cause a continuing change in the effective height of the plow
iv. Abrasive materials, such as pelletized taconite, cause objectionably rapid wear of the plow.

is, then, an object of the present invention to effect a reduction of the thickness of bulk material which must be present on a conveyor to assure thickness-independent response of a neutron-reflection moisture gauge, in order to bring the required thickness within that normally obtainable for most practicable conveyors.

It is a further object of the invention to provide a moisture measurement that, by not requiring ploughing, does not change the degree of compaction of the material.

In a broad aspect this invention is a neutron-reflection gauge for determining moisture content in bulk material comprising a neutron emitting means for positioning proximate to said bulk material to produce neutron radiation having a mean energy less than three million electron volts and a maximum neutron energy of less than five million electron volts, thereby causing the emission of thermal neutrons by said bulk material, a thermal neutron detector located adjacent to said transport system for detecting neutrons thermalized by said bulk material, radiation shielding for isolating said neutron emitting means from said thermal neutron detector, and indicator means connected to said detector to display a signal indicative of moisture content of the bulk material. Specific neutron sources which can be used in the neutron emitting means include lithium-7, which has a mean energy of about 300,000 KeV and a maximum energy of about 1.3 MeV, oxygen-18 which has a mean energy of about 2.4 MeV and a maximum energy of about 4.8 MeV, the radioisotopes of fluorine which have mean energies of about 1.4 MeV and maximum energies of about 3.5 MeV, and the radioisotopes of boron, which have mean energies of about 2.7 MeV and maximum energies of near 5 MeV.

Low energy neutron emitters have been employed in moisture measurement gauges which effect measurement by determining the neutron transmission characteristics of the bulk material measured rather than the neutron reflection characteristics, or backscatter as it is sometimes called, as in the present invention. An example of such a moisture measurement gauge operating by virtue of neutron transmission is the device depicted in U.S. Pat. No. 3,794,843. This type of device has several disadvantages when compared with a neutron-reflection moisture gauge, however. It requires equipment to be placed on opposite sides of the bulk material to be measured. This is frequently impractical in bulk conveyor or bulk storage systems because of space limitations and/or inaccessibility to one or more of the sides of the bulk material. Also, fluctuating density of the bulk material makes a density measurement gauge a necessary adjunct of a neutron transmission moisture measurement gauge, as has previously been explained.

The invention may be more clearly explained with reference to the accompanying drawings in which.

Figure 1:
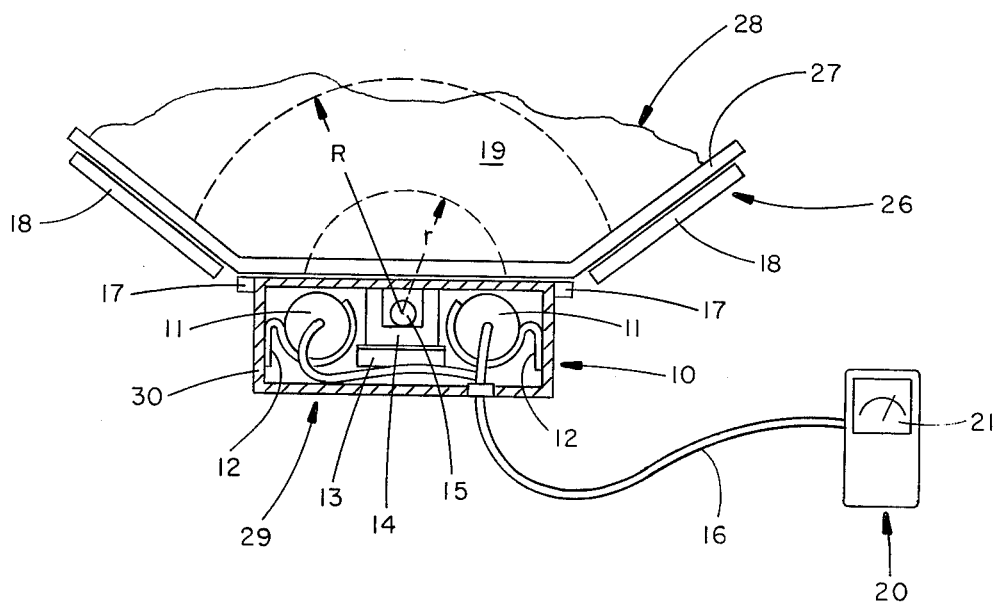
FIG. 1 is a cross-sectional view of a belt conveyor employing the present invention.

Referring now to FIG. 1, there is depicted a belt conveyor transport system 26 employing a trough shaped conveyor belt 27 supported from beneath by rollers 17 and supported at its sides by rollers 18. Bulk material 19 is carried by the bulk transport system 26 past a moisture measurement gauge 10. The geometrical distribution of bulk material 19 at the particular cross-section of the belt depicted in FIG. 1 is indicated by the boundary 28. It is to be understood that the boundary 28 is not uniform throughout the length of the belt conveyor system 26, but may undergo large variations.

The moisture measurement gauge 10 is comprised of an irradiation and detection sensor unit 29 and a moisture indication meter 20. The irradiation and detection unit 29 utilizes a rectangular metal container 30 positioned between rollers 17 located along the length of the conveyor belt 27. Conventional detector tubes 11 are fastened to container 30 by means of brackets 12 welded to the sides of container 30. These detector tubes are typically $^{10}BF_3$ tubes or $^3He$ tubes. A typical $^3He$ tube is described in detail in U.S. Pat. No. 3,240,971. The detector tubes are electrically connected to the moisture indicating meter 20 by means of cables enclosed within the cable harness 16. A radiation source of neutrons 15 is positioned adjacent to the transport belt 27. The thermal neutron detector tubes 11 are shielded from the source 15 by radiation shielding material 14, typically formed of a layer of lead to absorb any electro-magnetic radiation and a layer of a compound of boron, lithium or other element of high thermal neutron absorption which is mounted on container 30. The radiation shielding material 14 prevents the thermal neutron detector tubes 11 from being actuated directly by the radiation source 15, so that the thermal neutron detectors 11 are responsive almost exclusively to thermal neutrons generated in the bulk material 19.

In the preferred embodiments, the radiation source 15 is comprised of an intimate mixture of a target material containing the isotope lithium-7, the isotope oxygen 18, boron or fluorine, together with an alpha emitting source material, such as americium-241 or plutonium-238.

Alpha rays from the source material strike the target material in the source 15, thereby inducing a nuclear reaction which produces neutrons. When this target material is Li-7, O-18, F, or B, the resulting "fast" neutrons have a mean energy of less than 3 MeV and a maximum energy of less than 5 MeV. In contrast, radioactive neutron sources conventionally used in moisture measuring gauges employ beryllium target material instead of lithium or are made entirely from the spontaneously fissioning isotope californium-252. These neutron sources produce neutrons which have mean energies of about 4.5 MeV and 2.3 MeV, respectively, and maximum neutron energies in excess of 10 MeV.

Neutrons from the source 15 pass into the bulk process material 19, and some of the neutrons are thermalized and are scattered back to the detectors 11, this thermalization having been accomplished by repeated collisions with the hydrogen nucleii in the water contained in the bulk material 19. The flux of thermal neutrons at the detectors 11 is proportional to the volumetric concentration of hydrogen in the material, or to moisture content if there is no hydrogen in the material other than that associated with the moisture. The responses of the detectors 11 are strongly biased in favor of thermal neutrons. The outputs of the detectors 11 are therefore indicative of the total hydrogen content, and if no other hydrogen is present in the bulk material 19, to the moisture content of the bulk material 19.

Thermalized neutrons which reach the detector are the result of interaction in a roughly hemispherical volume of bulk process material whose apparent radius depends upon the density and moisture content of the material and upon the effective energy of the neutrons from the radioactive source 15. Neutrons which escape this volume have little chance of reaching the detectors since increasing the neutron energy increases the number of events required for thermalization. The radius of this hemisphere of influence increases with increasing neutron energy. Changing the density and moisture content of the material and changing the effective neutron energy can change the radius of the hemisphere of influence from a few inches or as great as a few feet. The relative radii of the respective hemispheres of influence of a source using beryllium target material and a source using lithium target material are indicated by R and r respectively in FIG. 1. It can be seen that use of a radioactive source which uses beryllium target material will involve an error due to variations in the geometrical distribution of the bulk material 19 when the bulk material is in the configuration indicated at 28. This is because there is a vacancy in the distribution of bulk material 19 lying within the radius R. To the contrary, the radioactive source 15 of the present invention employing lithium target material will not produce such an error since the radius r encompasses no such vacancy. In general, any vacancy which might occur will create a greater percentage effect in the material present within R than within r. Because of the typical loading patterns of bulk conveyor systems as previously discussed, this difference in effective radius is particularly significant. In most cases of practical interest, belt loading is not great enough to give a thickness of bulk process material which is greater than the radius of influence (R) of neutrons from a beryllium target type neutron source. The use of the lower energy neutron source, such as lithium-7, oxygen-18, and the radioisotopes of fluorine and boron, with its smaller radius of influence 9r) permits moisture measurements to be made which are not sensitive to normal variations in the geometric distribution of bulk material on the belt 27.

Figure 2:
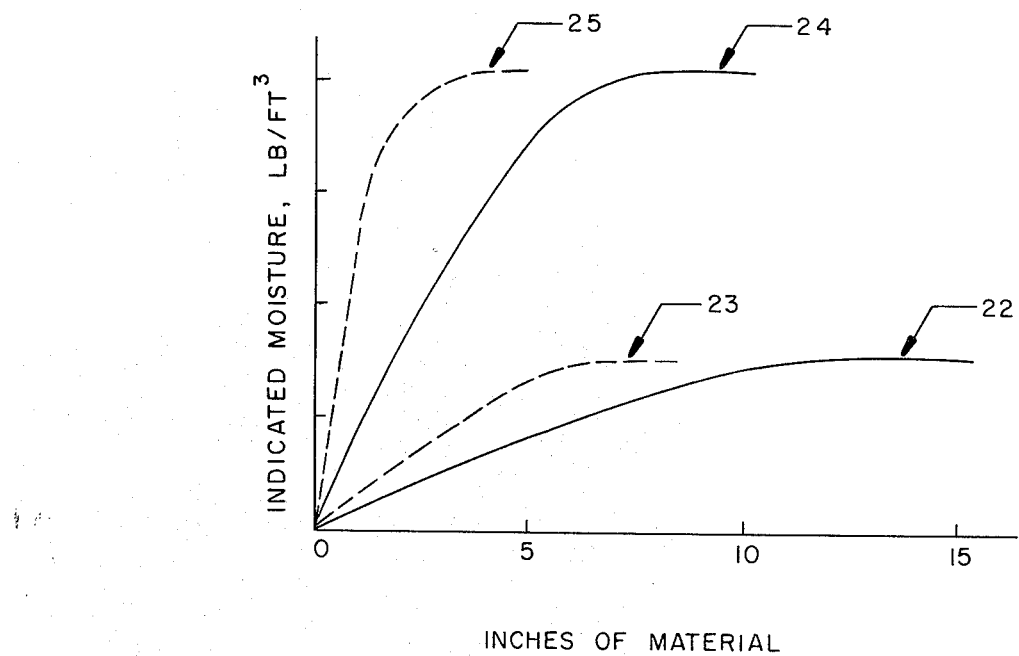
FIG. 2 is a graph showing the comparative results of moisture measurement using prior art devices and the gauge of the present invention.

In FIG. 2, results are depicted from the alternate use of a lithium target source and a beryllium target source in the system of FIG. 1. Bulk material 19 having a constant moisture content is carried by the belt 27. Ideally, the moisture reading would remain constant independent of the depth of the bulk material 19 in the belt 27. It will be seen, however, that the indicated moisture content depends upon the thickness of the layer of material in the vicinity of the sensor, unless the thickness exceeds a critical value, herein called the saturation thickness, in which case the response of the gauge to moisture becomes independent of the thickness of the layer of material. It will be evident that if the conveyor cannot be loaded to the saturation thickness, then thickness-independent response to moisture can be achieved only if the thickness of the material moving past the sensor is held constant. It can be seen that several inches of material is required before the curve 22 corresponding to the moisture gauge using a beryllium target source becomes constant (levels off). However, curve 23, corresponding to the gauge meter indication using a lithium target source, becomes constant (levels off) at about one half the bulk material 19 depth required to obtain constancy with the beryllium target source. The thickness required using an americium-beryllium source exceeds the loading limits of most conveyors. Therefore, it has heretofore been necessary to level the material on the conveyor, by means of a scraper-blade or plow above the conveyor, in order to achieve a uniform thickness of the material moving past the moisture sensor of a neutron-reflection gauge. Since there are numerous practical considerations which make plowing undesirable, the use of the neutron-reflection moisture gauge for measurement of materials on conveyors has, heretofore, been limited to those relatively rare cases in which unusually great conveyor loading could be achieved or the material on the conveyor could be plowed to uniform thickness. The comparison of results is even more significant when the moisture content of the material is increased and held at a much higher constant level. The curve 25 indicates that when the moisture content of the bulk material 19 is high, only about one third of the depth is required for the indicator 21 to become insensitive to geometric distribution of the bulk material using a lithium target source as contrasted with a gauge using a beryllium target source, as is apparent from curve 24 in FIG. 2. It is apparent that the improved radiation source of the present invention has very significant practical advantages over conventional radioactive sources in moisture measurement gauges.

The foregoing description and illustrations should not be considered limiting to the present invention, as various modifications thereof will be readily apparent to those familiar with moisture measurement of bulk materials.

I claim:

1. A neutron-reflection gauge for determining moisture content in moving bulk material comprising a neutron emitting means for stationary positioning proximate to said moving bulk material to produce neutron radiation having a mean energy less than three million electron volts and a maximum neutron energy of less than five million electron volts, said means thereby causing the emission of thermal neutrons by said bulk material, a thermal neutron detector located in a fixed position adjacent to said moving bulk material and said stationary neutron emitting means for detecting neutrons thermalized by said bulk material and impinging directly upon said detector, radiation shielding for isolating said neutron emitting means from said thermal neutron detector, and indicator means connected to said detector to display a signal indicative of moisture content of the aforesaid bulk material.

2. The moisture measurement gauge of claim 1 wherein the neutron emitting means is comprised of an intimate mixture of a compound containing the isotope lithium-7 and an alpha emitter.

3. The moisture measurement gauge of claim 2 wherein the alpha emitter is americium-241.

4. The moisture measurement gauge of claim 2 wherein the alpha emitter is plutonium-238.

5. A neutron-reflection gauge for determining moisture content in moving bulk material comprising a neutron emitting means including an intimate mixture of a compound of fluorine and an alpha emitter for stationary positioning proximate to said moving bulk material to produce neutron radiation, said means thereby causing the emission of thermal neutrons by said bulk material, a thermal neutron detector located in a fixed position adjacent to said stationary neutron emitting means for detecting neutrons thermalized by said bulk material, radiation shielding for isolating said neutron emitting means from said thermal neutron detector, and indicator means connected to said detector to display a signal indicative of moisture content of the aforesaid bulk material.

6. A neutron-reflection gauge for determining moisture content in moving bulk material comprising a neutron emitting means including an intimate mixture of a compound of boron and an alpha emitter for stationary positioning proximate to said moving bulk material to produce neutron radiation, said means thereby causing the emission of thermal neutrons by said bulk material, a thermal neutron detector located in a fixed position adjacent to said stationary neutron emitting means for detecting neutrons thermalized by said bulk material, radiation shielding for isolating said neutron emitting means from said thermal neutron detector, and indicator means connected to said detector to display a signal indicative of moisture content of the aforesaid bulk material.

7. A neutron-reflection gauge for determining moisture content in moving bulk material comprising a neutron emitting means including an intimate mixture of a compound containing the isotope oxygen-18 and an alpha emitter for stationary positioning proximate to said moving bulk material to produce neutron radiation, said means thereby causing the emission of thermal neutrons by said bulk material, a thermal neutron detector located in a fixed position adjacent to said stationary neutron emitting means for detecting neutrons thermalized by said bulk material, radiation shielding for isolating said neutron emitting means from said thermal neutron detector, and indicator means connected to said detector to display a signal indicative of moisture content of the aforesaid bulk material.

8. A moisture measurement gauge adapted for use in measurement of solid material on a belt transport system comprising a radiation source of neutrons positioned adjacent to a transport belt and including an intimate mixture of a compound containing the isotope lithium-7 and an alpha emitter, a thermal neutron detector located adjacent to the aforesaid transport belt, and indicator means connected to said detector for indicating moisture content of said solid material.

9. A moisture measurement gauge adapted for use in measurement of solid material on a belt transport system comprising a radiation source of neutrons positioned adjacent to a transport belt and including an intimate mixture of a compound of fluorine and an alpha emitter, a thermal neutron detector located adjacent to the aforesaid transport belt, and indicator means connected to said detector for indicating moisture content of said solid material.

10. A moisture measurement gauge adapted for use in measurement of solid material on a belt transport system comprising a radiation source of neutrons positioned adjacent to a transport belt and including an intimate mixture of a compound of boron and an alpha emitter, a thermal neutron detector located adjacent to the aforesaid transport belt, and indicator means connected to said detector for indicating moisture content of said solid material.

11. A moisture measurement gauge adapted for use in measurement of solid material on a belt transport system comprising a radiation source of neutrons positioned adjacent to a transport belt and including an intimate mixture of a compound containing the isotope oxygen-18 and an alpha emitter, a thermal neutron detector located adjacent to the aforesaid transport belt, and indicator means connected to said detector for indicating moisture content of said solid material.

12. The moisture measurement gauge of claim 5 wherein the alpha emitter is americium-241.

13. The moisture measurement gauge of claim 5 wherein the alpha emitter is plutonium-238.

14. The moisture measurement gauge of claim 6 wherein the alpha emitter is americium-241.

15. The moisture measurement gauge of claim 6 wherein the alpha emitter is plutonium-238.

16. The moisture measurement gauge of claim 7 wherein the alpha emitter is americium-241.

17. The moisture measurement gauge of claim 7 wherein the alpha emitter is plutonium-238.

18. The moisture measurement gauge of claim 8 wherein radiation shielding is interposed between said radiation source and said detector.

* * * * *